United States Patent

Beck et al.

[11] 4,013,674
[45] Mar. 22, 1977

[54] N-(1,2,2,2-TETRACHLOROETHYL)-FORMIMIDE-CHLORIDE FOR SYNTHESIZING TRICHLOROTHIAZOLE

[75] Inventors: Gunther Beck; Helmut Heitzer, both of Leverkusen, Germany

[73] Assignee: Bayer Aktiengesellschaft, Leverkusen, Germany

[22] Filed: Dec. 9, 1975

[21] Appl. No.: 639,137

[30] Foreign Application Priority Data

Dec. 12, 1974 Germany .......................... 2458827
Dec. 12, 1974 Germany .......................... 2458825

[52] U.S. Cl. ...................... 260/302 R; 260/561 R; 260/566 D
[51] Int. Cl.[2] ....................................... C07D 263/30
[58] Field of Search ................... 260/566 D, 302 R

*Primary Examiner*—R. Gallagher
*Attorney, Agent, or Firm*—Burgess, Dinklage & Sprung

[57] ABSTRACT

The new compound N-(1,2,2,2-tetrachloroethyl)-formimide chloride of the formula

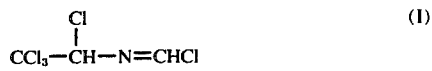

is produced by reacting a substituted formamide of the formula

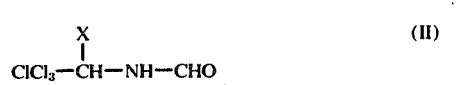

wherein
X is OH or Cl, with approximately the stoichiometrically required amount of a highly reactive inorganic acid chloride, e.g. phosphorus pentachloride. The compound (I) can be reacted with sulfur at about 150° to 250° C to produce trichlorothiazole of the formula

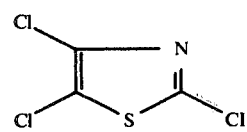

which is known to have insecticidal activity.

15 Claims, No Drawings

N-(1,2,2,2-TETRACHLOROETHYL)-FORMIMIDE-CHLORIDE FOR SYNTHESIZING TRICHLOROTHIAZOLE

The invention relates to N-(1,2,2,2-tetrachloroethyl)-formimide-chloride, a process for its preparation, and its use in preparing trichlorothiazole.

A process for the preparation of trichlorothiazole is known (see U.S. Pat. No. 3.833.601 = German Published Specification DOS No. 2,213,865).

The starting compounds used therein, namely pentachloro-ethylisocyanide-dichloride or trichlorovinyl-isocyanide-dichloride, can only be prepared in low yield and/or by multi-stage synthesis. A further disadvantage of this process is that considerable amounts of disulfur dichloride arise as an undesired by-product.

It has been found that N-(1,2,2,2-tetrachloroethyl)-formimide-chloride of the formula

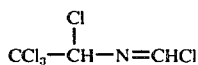

(I)

is obtained when substituted formamides of the general formula

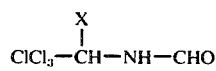

(II)

wherein
X is OH or Cl,
optionally mixed with an inert diluent, are reacted with approximately the stoichiometrically required amount of a highly reactive inorganic acid chloride.

Inert diluents which can be used for the process according to this step are all solvents which, under the reaction conditions, do not react with the acid chlorides used. Optionally chlorinated, aliphatic and aromatic hydrocarbons, especially those containing up to about 8 carbon atoms, such as hexane, heptane, benzene, toluene, chloroform, carbon tetrachloride, 1,2-dichloroethane, 1,1,2,2-tetrachloroethane, trichloroethylene, tetrachloroethylene and chlorobenzene, and also aliphatic open-chain or cyclic ethers, such as diethyl ether, tetrahydrofuran and dioxane, as well as thionyl chloride and phosphorous oxychloride may be mentioned. In general, about 0.5 to 20, preferably about 1 to 10, parts by volume of diluent are used per part by weight of (II). Particularly preferred diluents are carbon tetrachloride, phosphorus oxychloride and thionyl chloride.

Highly reactive inorganic acid chlorides which can be used for the process according to this step are phosphorus pentachloride (or an equimolar mixture of phosphorus trichloride and chlorine), as well as thionyl chloride to which about 0.01 to 10, preferably about 0.1 to 1, per cent by volume of an N-lower alkyl-substituted amide of a lower carboxylic acid such as formic, acetic, butyric or carbamic acids, for example dimethylformamide, methylformamide, dimethylacetamide, N-methylpyrrolidone or tetramethylurea, have been added. Preferred acid chlorides are phosphorus pentachloride and also thionyl chloride to which about 0.1 to 1 per cent by volume of dimethylformamide has been added.

The process according to this step may be explained in more detail, using, for example, phosphorus pentachloride as the acid chloride, with the aid of the following equations:

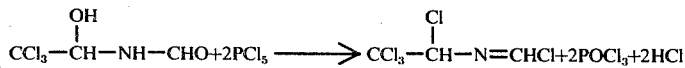

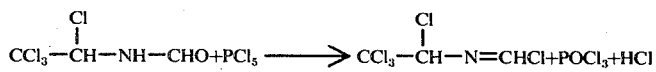

It has further been found that this material (I) can be reacted with sulfur at a temperature of about 150° to 250° C, preferably about 170° to 230° C, to produce trichlorothiazole of the formula

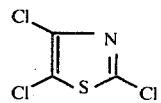

(III)

in accordance with the equation

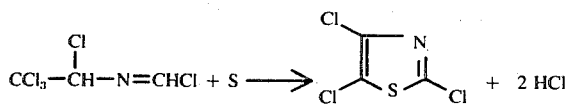

The production of the formimide-chloride (I) can be carried out at a temperature of about 0° to 150° C, preferably at a temperature of about 10° to 80° C. The starting materials for this reaction of the formula (II), are known (chloralformamide: Ber. dtsch. chem. Ges. 45, 945; N-(1,2,2,2-tetrachloroethyl)-formamide: Ber. dtsch. chem. Ges. 47, 1,180).

In order to achieve a complete conversion, in general at least the stoichiometrically required amount of acid chloride is used for the process according to this step, for example at least about 2 moles of $PCl_5$ for the reaction of chloral-formamide or at least about 1 mole of $PCl_5$ for the reaction of N-(1,2,2,2-tetrachloroethyl)-formamide. Appropriately, the acid chloride is employed in excess, for example up to about 1.2 times the stoichiometrically required amount. An excess of between about 2 and 20 mole % above the stoichiometrically required amount of acid chloride is preferred, for example about 2.04 to 2.4 moles of acid chloride per mole of the formamide in the reaction of chloral-formamide with $PCl_5$ and about 1.02 to 1.2 moles of acid chloride per mole of the formamide in the reaction of N-(1,2,2,2-tetrachloroethyl)-formamide with $PCl_5$.

To carry out the process, one of the starting materials (II) can first be mixed with the acid chloride, in the abovementioned molar ratio, appropriately at room temperature or slightly above (for example up to about 35° C). Insofar as the batch quantities are small (for example up to about 10–30 g of starting material (II)), the starting material (II) and the acid chloride can be mixed directly with one another and the use of a diluent can be dispensed with. When phosphorus pentachloride is used as the acid chloride, the reaction is further facilitated by the fact that phosphorus oxychloride, which is suitable as the diluent and which ensures simpler control of the course of the reaction (improved possibilities for thorough mixing and, if necessary, heat removal), is formed during the reactions according to the process of this step. The liquid end product (I) formed during the reaction also has a similar effect. With larger batches, however, it is appropriate both to carry out the reaction in the presence of a diluent and to allow the two reactants to react with one another in small proportions. Preferably, the diluent is initially introduced together with one of the reactants, for example the acid chloride (it being possible in the case of thionyl chloride for the diluent and the acid chloride to be identical to one another), and the other reactant is then metered in in small portions. The mixture is then warmed to the indicated temperature range, an upper temperature limit of about 80° C particularly preferentially not being exceeded. Of course, it is also possible to heat the reaction mixture to temperatures above 80° C; however, in this case, the formation of byproducts, for example those with a higher chlorine content, takes place to an increasing extend and although it is possible to separate these from N-(1,2,2,2-tetrachloroethyl)-formimide-chloride (I), according to the invention, without difficulty, for example by fractional vacuum distillation through a column, this is more expensive.

It has proved advantageous to reduce the concentration, in the reaction mixture, of dissolved hydrogen chloride, which is formed by the process according to this step. This can be effected, for example, in a simple manner by passing a gas, which is insert under the reaction conditions, through the reaction mixture during the entire reaction period or part thereof. Examples of inert gases of this type are nitrogen and, of course, also rare gases such as argon; if the particularly preferred upper temperature limit of about 80° C is not exceeded, chlorine can also be employed.

When phosphorus pentachloride is used as the acid chloride, it can be advantageous, when the reaction is complete, to destroy any slight surplus which may still be present by passing in sulfur dioxide, in accordance with the known reaction

$PCl_5 + SO_2 \rightarrow POCl_3 + SOCl_2$

N-(1,2,2,2-Tetrachloroethyl)-formamide, which, in addition to chloral-formamide, is used as a starting material, can be prepared from chloral-formamide (IV) by reaction with phosphorus pentachloride (compare Ber. dtsch. chem. Ges. 47, 1,180) or thionyl chloride (British Patent Specification No. 993,051). This reaction can be described, for example, by the following reaction equation:

in first isolating as such the starting compound N-(1,2,2,2-tetrachloroethyl)-formamide (V), which has been prepared in the abovementioned manner and which decomposes very readily in the air.

The preparation of N-(1,2,2,2-tetrachloroethyl)-formimide-chloride (I), according to the invention, on the basis of chloral-formamide (IV), in the "one-pot" process, that is to say without intermediate isolation of N-(1,2,2,2-tetrachloroethyl)-formamide (V), is therefore particularly preferred.

N-(1,2,2,2-Tetrachloroethyl)-formimide-chloride of the formula (I), according to the invention, is new and is a colorless liquid which can be distilled in vacuo without decomposition but which is sensitive to moisture, so that moisture has to be excluded as completely as possible during the preparation and storage thereof.

The compound (I) is a valuable, highly reactive intermediate for producing trichlorothiazole by reaction with at least an equimolar amount of sulfur to achieve as complete conversion to (III) as possible; suitably, for example, up to about 80% excess of sulfur can be used. Preferably, an amount which ranges from the stoichiometrically required amount of sulfur to about 1.8 times this amount is employed for the reaction.

It is to be regarded as extremely surprising that it is possible, by means of the process according to the invention, to prepare N-(1,2,2,2-tetrachloroethyl)-formimide-chloride, of the formula (I), which is not salt-like and which can be distilled in vacuo without decomposition, in yields of up to more than 95% of theory. In fact, no single N-monoalkyl-formimide chloride, of the general formula alkyl-N=CHCl and of a proven structure, which is not salt-like and can be distilled, has yet been described in the literature.

It is also extremely surprising that the imidechloride (I), mixed with sulfur, when exposed to a temperature of about 200° C forms trichlorothiazole (III) in a yield of between 80 and 90% of theory, since it is known from U.S. Pat. No. 3,282,923 that such imide-chlorides are very prone to decomposition reactions.

Compared to the processes of preparation of trichlorothiazole (III) according to U.S. Pat. No. 3,833,601, the process according to the invention has the advantage that it starts from N-(1,2,2,2-tetrachloroethyl)-formimide-chloride as an easily accessible starting compound and that the production of disulfur dichloride is avoided.

Trichlorothiazole of the formula (III) is known from U.S. Pat. No. 3,833,601 to exhibit insecticidal properties.

If desired, the reaction of the imide-chloride (I) with sulfur to produce trichlorothiazole (III) can be conducted without full or even partial purification of (I), directly using the reaction mass in which it was prepared.

The invention will be further described in the following illustrative examples wherein all parts are by weight unless otherwise recited.

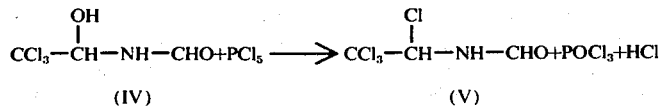

$$CCl_3-\underset{\underset{\text{(IV)}}{|}}{\overset{\overset{\text{OH}}{|}}{CH}}-NH-CHO + PCl_5 \longrightarrow CCl_3-\underset{\underset{\text{(V)}}{|}}{\overset{\overset{\text{Cl}}{|}}{CH}}-NH-CHO + POCl_3 + HCl$$

In the process according to this step, it is optional whether the starting compounds of the general formula II are reacted with phosphorus pentachloride or with thionyl chloride. There is thus no advantage when actually carrying out the process according to the invention

EXAMPLE 1 a. 400 g (2.08 moles) of chloral-formamide are added in small portions, with the exclusion of moisture, in the course of about 2 hours to a suspension of 1,000 g (4.8 moles) of phosphorus pentachloride in 2,000 ml of carbon tetrachloride, which has been warmed to about 32° to 36° C. Without further heating, the internal temperature remains between about 32° and 36° C. The mixture is then warmed up to 60° C in the course of about 1 hour. The excess phosphorus pentachloride is then destroyed at between 30° and 50° C by passing in sulfur dioxide for 0.5–1 hour. After stripping off the diluent as well as phosphorus oxychloride and thionyl chloride in vacuo, 440 g (corresponding to 92% of theory) of N-(1,2,2,2-tetrachloroethyl)-formimide-chloride, which is pure according to gas chromatograhy and has the structure

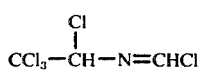

is obtained at 89° to 90° C/12 mm Hg as the cis-trans mixture. Distillation residue 6–8 g. The empirical formula $C_3H_2Cl_5N$ is confirmed by the mass spectrum.

The strongest infrared bands are at 1,650, 1,300, 820, 765 and 750 cm$^{-1}$.

The $^1$H NMR spectrum (without solvent) at 60 MHz using TMS as the internal standard, measured at about 40° C, shows 4 doublets:

1. $\delta = 6.00$ ppm, d, $J = 1.5$ Hz
2. $\delta = 6.22$ ppm, d, $J = 1.9$ Hz
3. $\delta = 8.10$ ppm, d, $J = 1.5$ Hz
4. $\delta = 8.61$ ppm, d, $J = 1.9$ Hz (1) and (2) are assigned to the portion at the tetrachloroethyl group and (3) and (4) are assigned to that of the formimide group. The ratio of the intensities of (1):(2) and of (3):(4) is 75:25 in each case.

(b). The procedure is analogous to (a), the difference being that 2,500 ml of chloroform are employed in place of 2,000 ml of carbon tetrachloride. The yield of N-(1,2,2,2-tetrachloroethyl)-formimide-chloride is practically identical to that Example 1a.

EXAMPLE 2

1,040 g (5 moles) of phosphorus pentachloride in 2,000 ml of carbon tetrachloride are first reacted with 450 g (2.34 moles) of chloral-formamide analogously to Example 1. The mixture is then heated up to 85° C. Working up is carried out as described in Example 1. By means of a single distillation, 469 g of distillate, which according to gas chromatographic analysis contains 435 g (corresponding to 81% of theory) of N-(1,2,2,2-tetrachloroethyl)-formimide-chloride and 10 g of a more highly chlorinated product, are obtained in the boiling range from 85° to 96° C/14 mm Hg. By means of subsequent fractional vacuum distillation in a column with a dephlegmator, N-(1,2,2,2-tetrachloroethyl)-formimide-chloride in more than 99% purity is easily obtained. Boiling point 89°–90° C/12 mm Hg.

EXAMPLE 3

45 g (0.234 mole) of chloral-formamide are added in small portions in the course of half an hour, at between 20 and 25° C, with exclusion of moisture, to a suspension of 104 g (0.5 mole) of phosphorus pentachloride in 250 ml of carbon tetrachloride. A fast stream of chlorine (such that the waste gas has a distinct greenish coloration) is then passed through the reaction mixture for about 3 hours, while heating gradually up to 78° C. Working up according to Example 1 gives, in the range from 64° to 92° C/15 mm Hg (bridge distillation), 54 g of distillate, which according to gas chromatographic analysis consists to the extent of 95.2% of N-(1,2,2,2-tetrachloroethyl)-formimide-chloride (corresponding to a yield of 95.7% of theory) and to the extent of 2.5% of a more highly chlorinated product.

EXAMPLE 4

(a) 135 g (0.7 mole) of chloral-formamide are added in small portions, with exclusion of moisture, to a suspension of 312 g (1.5 moles) of phosphorus pentachloride in 500 ml of phosphorus oxychloride, at between 20° and 30° C in the course of about one hour, while cooling with ice and while passing in a fast stream of dry nitrogen.

When the addition of the chloral-formamide is complete, the mixture is heated up to 81° C in about 2 hours, while continuing to pass nitrogen through the mixture. After passing in sulfur dioxide for about one hour at about 45° to 65° C, the mixture is fractionated using a bridge. After stripping off the phosphorus oxychloride, 161 g of distillate (residue 4 g) which, according to gas chromatographic analysis, contains 5 g of POCl$_3$, 141 g (corresponding to 88% of theory) of N-(1,2,2,2-tetrachloroethyl)-formimide-chloride and 15 g of a more highly chlorinated product, are obtained above 96° C up to a sump temperature of 150° C at 16 mm Hg.

(b) 135 g (0.7 mole) of chloral-formamide are added, with exclusion of moisture, in the course of 30 minutes at between 20° and 25° C to a suspension of 300 g (1.44 moles) of phosphorus pentachloride in 500 ml of phosphorus oxychloride, while cooling with ice and while passing in a fast stream of nitrogen. The virtually clear solution is then fractionated direct. After stripping off the bulk of the phosphorus oxychloride in a water pump vacuum, 151 g of distillate (residue 7 g), which according to the gas chromatogram contains 4 g of phosphorus oxychloride, 139 g (corresponding to 86.5% of theory) of N-(1,2,2,2-tetrachloroethyl)-formimide-chloride and 4 g of a more highly chlorinated product, are obtained at 96°–105°/16 mm Hg.

EXAMPLE 5

(a) 500 g (2.6 moles) of chloral-formamide are added in the course of one hour to a mixture of 2,000 ml of thionyl chloride and 2 ml of dimethylformamide, at about 30° C, with exclusion of moisture. The mixture is then heated to the reflux temperature (about 77° C) for about 3.5 hours. After the excess thionyl chloride has been stripped off, fractional distillation using a bridge gives, about 96° C/18 mm Hg up to a bath temperature of about 200° C, 354 g of distillate, which, in addition to higher-boiling products, according to gas chromatographic analysis contains 81.3% (corresponding to a yield of 48% of theory) of N-(1,2,2,2-tetrachloroethyl)-formimide-chloride, the distillation residue being 109 g.

(b) The procedure is analogous to (a), the difference being that N-(1,2,2,2-tetrachloroethyl)-formamide is used in place of chloral-formamide. The yield of N-(1,2,2,2-tetrachloroethyl)-formimide-chloride is approximately the same (about 45 % of theory) as under (a).

EXAMPLE 6

100 g (0.436 mole) of N-(1,2,2,2-tetrachloroethyl)-formimide-chloride of the formula CCl₃—CHCl—N=CHCl are heated with 25 g (0.78 mole) of sulfur, with exclusion of moisture, in a three-necked flask fitted with a stirrer, a thermometer and a reflux condenser. Incipient evolution of hydrogen chloride gas is observed at about 170° C and vigorous evolution at about 180°–185° C; this evolution has subsided after about 1 hour. The temperature of the heating bath is now adjusted to about 220° to 240° C and the mixture is heated under reflux (internal temperature initially about 200° C, then falling to about 190° C) until the IR spectrum of the reaction mixture no longer shows any absorption at about 1,650 cm⁻¹. According to the findings of the IR spectrum, more than 90% conversion is already achieved about 8 hours after the start of the reaction; a further 8–12 hours are then again required until the IR band at about 1,650 cm⁻¹ has completely disappeared. When the reaction is complete, the mixture is first distilled over a bridge, in a water pump vacuum, up to a sump temperature of about 250° C until no further distillate passes over and the distillate is then again fractionated in a column. At a boiling point of 76°–78° C/12 mm Hg, 72 g (corresponding to 86.5% of theory) of pure trichlorothiazole of the formula

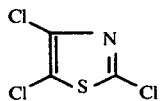
(III)

all the properties of which are identical to those of the product obtained according to U.S. Pat. No. 3,833,601, are obtained.

It will be appreciated that the instant specification and examples are set forth by way of illustration and not limitation, and that various modifications and changes may be made without departing from the spirit and scope of the present invention.

What is claimed is:

1. N-(1,2,2,2-tetrachloroethyl)-formimide-chloride of the formula

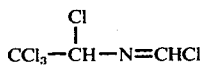

2. A process for the preparation of N-(1,2,2,2-tetrachloroethyl)-formimide-chloride according to claim 1, comprising contacting a formamide of the formula

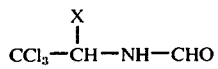

wherein
X is OH or Cl,
with approximately the stoichiometrically required amount of a highly reactive inorganic acid chloride.

3. The process according to claim 2, wherein phosphorus pentachloride or an equimolar mixture of phosphorus trichloride and chloride is used as the acid chloride.

4. The process according to claim 2, wherein thionyl chloride containing about 0.01 to 10 % by volume of an N-alkyl-substituted aliphatic acid amide is used as the acid chloride.

5. The process according to claim 2, wherein the acid chloride is employed in about 1 to 1.2 times the stoichiometrically required amount.

6. The process according to claim 2, wherein the reaction temperature is about 0° to 150° C.

7. The process according to claim 2, wherein the reaction temperature is about 10° to 80° C.

8. The process according to claim 2, wherein a gas which is inert under the reaction conditions is passed through the reaction mixture during the reaction.

9. The process according to claim 2, wherein the reaction is effected in the presence of an inert diluent.

10. The process according to claim 5, wherein the acid chloride is selected from the group consisting of phosphorus pentachloride, an equimolar mixture of phosphorus trichloride plus chlorine, and thionyl chloride containing about 0.01 to 10 % by volume of an N-alkyl-substituted aliphatic acid amide, and the reaction is effected in an inert diluent selected from the group consisting of carbon tetrachloride, phosphorus oxychloride and thionyl chloride at a temperature from about 10° to 80° C while passing through the reaction mixture a gas which is inert under the reaction conditions.

11. A process for the preparation of trichlorothiazole of the formula

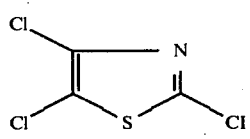

comprising reacting N-(1,2,2,2-tetrachloroethyl)-formimide-chloride of the formula

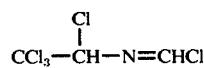

with sulfur in the temperature range from 150° to 250° C.

12. The process according to claim 11, wherein the reaction is carried out at a temperature of about 170° to 230° C.

13. The process according to claim 11, wherein the reaction is carried out with about 1 to 2 times the stoichiometrically required amount of sulfur.

14. The process according to claim 11, wherein the N-(1,2,2,2-tetrachloroethyl)-formimide chloride is produced by contacting a formimide of the formula

wherein
X is OH or Cl,
with approximately the stoichiometrically required amount of a highly reactive inorganic acid chloride.

15. The process according to claim 11, wherein the reaction is carried out at a temperature of about 170° to 230° C in the presence of about 1 to 2 times the stoichiometrically required amount of sulfur, the N-

(1,2,2,2-tetrachloroethyl)-formimide chloride being produced by reacting a formimide of the formula

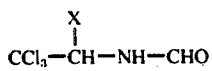

wherein
X is OH or Cl,
with about 1 to 1.2 times the stoichiometrically required amount of a highly reactive inorganic acid chloride selected from the group consisting of phosphorus pentachloride, an equimolar mixture of phosphorus trichloride plus chlorine, and thionyl chloride containing about 0.01 to 10 % by volume of an N-alkyl substituted aliphatic acid amide, and the reaction is effected in an inert diluent selected from the group consisting of carbon tetrachloride, phosphorus oxychloride and thionyl chloride at a temperature from about 10° to 80° C while passing through the reaction mixture a gas which is inert under the reaction conditions.

* * * * *